United States Patent [19]

Temple et al.

[11] Patent Number: 4,847,252

[45] Date of Patent: Jul. 11, 1989

[54] METHOD FOR ALLEVIATION OF VASCULAR HEADACHE

[75] Inventors: Davis L. Temple, Wallingford, Conn.; Michael F. Rafferty, Wheeling, Ill.; Michael S. Eison, Avon; Stacy N. Suberg, Farmington, both of Conn.

[73] Assignee: Bristol-Myers Company, New York, N.Y.

[21] Appl. No.: 262,556

[22] Filed: Oct. 25, 1988

[51] Int. Cl.$^4$ ............................................. A61K 31/50
[52] U.S. Cl. ................................................... 514/252
[58] Field of Search ......................................... 514/252

[56] References Cited

U.S. PATENT DOCUMENTS 4,411,901 10/1983 Temple, Jr. et al. .

OTHER PUBLICATIONS

Annual Reports in Medicinal Chemistry: vol. 21 (1986) pp 1-9 (1/25).
Annual Reports in Medicinal Chemistry: vol. 22 (1987) pp. 1-10; (1/25).
Eison, et al., "Drugs of the Future", 1985; 10(9), 773-772 (1/26).
Kurtz et al., "Review of Pre-Clinical and Clinical Pharmacology of Tiaspirone, an Atypical AD".NCDEU Abstract 1987 (1/28).
Drug Evaluations, 6th Edn, 1986, Chap. 13, pp. 239-252 (2/11).

*Primary Examiner*—Stanley J. Friedman
*Attorney, Agent, or Firm*—Richard P. Ryan

[57] ABSTRACT

Tiospirone and its pharmaceutically acceptable salts are useful in alleviation of vascular or vascular-related headaches such as migraine, cluster, muscle-contraction, and combined headaches.

10 Claims, No Drawings

METHOD FOR ALLEVIATION OF VASCULAR HEADACHE

FIELD OF THE INVENTION

This invention is concerned with a drug bio-affecting body-treating process which employs the benzisothiazole compound 8-[4-[4-(1,2-benzisothiazol-3-yl)-1-piperazinyl]-butyl]-8-azaspiro(4.5)decane-7,9-dione or a pharmaceutically acceptable acid addition salt thereof.

BACKGROUND OF THE INVENTION

The benzisothiazole compound with which the present invention is concerned has been given the USAN name of tiospirone. The hydrochloride salt has been referred to in the prior art as BMY-13859-1 and also as tiospirone. Other acid addition salts thereof are named by combining "tiospirone" with the appropriate word to define the acid form which it is prepared as in "tiospirone hydrochloride". The latter is the U.S. adopted name (USAN) which was recommended by the U.S. Pharmacopeial Convention, Inc.

The synthesis of the compound and disclosure of its antipsychotic properties are described in the following patent and representative publications.

1. Temple, Jr., et al., U.S. Pat. No. 4,411,901 issued Oct. 25, 1983.
2. Annual Reports in Medicinal Chemistry: Vol. 21 (1986) pp. 1–9; Vol. 22 (1987) pp. 1–10.
3. Eison, et al., BMY-13859. Drugs of the Future 1985; 10(9): 773–2.
4. Kurtz, et al., "Review of pre-clinical and clinical pharmacology of tiaspirone an atypical antipsychotic", NCDEU Abstract 1987.

Vascular headache is a recognized category of headache classification which generally is understood to contain migraine and cluster headaches due to a vascular implication in their etiology. Currently, it is thought possible that muscle-contraction headaches also contain a vascular component in their etiology and may therefore be considered as vascular-related. Additionally there are headaches which are classified as "combined" or "mixed" since they appear to be muscular and vascular-type occurring together. For a good current summary of headache and its treatment, see: Chapter 13: "Drugs Used to Treat Migraine and Other Headaches" in Drug Evaluations, 6th Edition, 1986, pp. 239–252, American Medical Association, W.B. Saunders Co., Phil., PA.

Drugs most commonly used in treatment of headache fall into the following groups:
Ergot Alkaloids,
Beta-blocking Agents,
Calcium Channel Blocking Agents,
Antidepressants, and
Mixtures of these.

Management of recurring vascular headache is complicated by the lack of a single therapy which is effective in all patients with the same headache type and by the need to select either an abortive or prophylactic method of treatment for these headaches. Further complication involves the current use of drugs that cause dependence with extended use, such as ergotamine. Another important consideration for the present invention is that the more effective antimigraine agents in current use, e.g. the ergots, methysergide, produce severe use-limiting side-effects with long term usage.

In short, there is no reliable method of treatment for patients afflicted with the more severe type of headache, classified as vascular headache. Further, there is nothing in the prior art to suggest the method of the present invention—that tiospirone would effectively alleviate such headaches, particularly when tiospirone bears no structural resemblance to any therapeutic agent accepted as being useful in the treatment of vascular headaches.

The objectives of the present invention have been to provide effective relief from the pain associated with vascular or vascular-related headache; to give prophylactic protection against headache episodes; to provide abortive therapy; and to provide headache relief using an agent not associated with drug dependence.

SUMMARY OF THE INVENTION

The method of the present invention is intended for the alleviation of vascular or vascular-related headache of which migraine and cluster are the best known specific examples. The method essentially involves administration of tiospirone, or a pharmaceutically acceptable salt thereof, to a human in need of such treatment. For use in the instant method, oral administration of tiospirone hydrochloride from about 40 to 200 mg per day in divided doses is anticipated as being the preferred dosage regimen.

DETAIL DESCRIPTION OF THE INVENTION

Frequent irregularly-occurring episodes of headache afflict a large number of people but are usually acute in nature and of short duration. Relief of this type of headache is typically provided by mild analgesics such as aspirin or acetaminophen. Such headaches are quite common and, while painful and perhaps annoying, are seldom incapacitating and debilitating. Chronic recurrent headaches of the vascular category, however, usually lead to patient consultation with a physician due to pain severity which is often incapacitating.

Although there is no universally accepted classification system for headache, vascular headache, for the purposes of the present invention, refers mainly to migraine and cluster headaches. Migraine includes the common or classical type as well as migraine variants which would be familiar to one skilled in the art. Other subtypes such as toxic vascular and hypertensive headaches, as well as some muscle-contraction and combined or mixed vascular-muscle headaches may also fall into a vascular-related headache category and be treatable by the present invention. It is appreciated by one skilled in the art that no single therapy is effective in all patients diagnosed with the same subtype of headache, thereby raising further uncertainties about headache classification.

The present invention results from the discovery that tiospirone hydrochloride provides effective relief to patients suffering from vascular headache, in particular active periods of cluster headache. There are the seasonal periods during which patients experience frequent episodes of cluster headache each day and, in many instances, such severe pain is associated with the episodes that hospitalization is required. For these patients, treatment objectives are to provide pain relief and decrease or eliminate further episodes of cluster headache. A third objective, met with tiospirone, is to provide treatment with an agent that does not cause drug dependence. Many of the agents used in vascular headache such as a barbiturates, antianxiety agents, ergotamine, narcotics, analgesic and caffeine mixtures can cause drug dependence and complicate headache management by withdrawal problems. While medications useful in cluster headache, such as methysergide and ergotamine, are also effective against migraine and other vascular headaches, it is recognized that an advantage in studying the cluster headache patient is that, "the placebo effect is small in cluster headache... (Cf: K. Ekbom, "Treatment of Cluster Headache" in *Migraine: Clinical and Research Aspects*, ed. J.N. Blau, p. 231)

In this regard, tiospirone hydrochloride was administered to six in-patients with a long history of cluster headache and currently experiencing a period of cluster headache. The treatment period of this open label study was 12 days and the course of the patient's condition was monitored by the clinical investigator who was familiar with each patient and their particular cluster headache history. The clinician's evaluation of tiospirone hydrochloride treatment response was based on reduction of the duration, severity or frequency of headaches. Severe headaches in these in-patients were treated with oxygen inhalation, lidocaine or antihistamines. The need for such therapeutic intervention was used as an additional parameter for assessment of tiospirone efficacy.

Two of the six patients were completely headache free by the last 3 study days, two others demonstrated a good response to treatment with over 50% reduction in headache frequency and the headaches were only of mild severity. The final two patients demonstrated some response in lessened severity. Given the nature of cluster headache, these clinical results indicate effective treatment of vascular headache with tiospirone hydrochloride.

In addition to the clinical results, tiospirone's pharmacology is also indicative of effectiveness in treating vascular headache. The agents most commonly used in treating vascular headaches have a pharmacologic component of serotonin antagonism. Tiospirone is a potent serotonin antagonist and, in addition, possesses dopamine antagonism. Dopamine antagonism is associated with producing an antiemetic effect which would be quite valuable in combating the nausea and vomiting associated with vascular headache attacks. Although tiospirone possesses dopaminergic antagonism activity, relevant preclinical and clinical data indicate that side-effect liabilities such as movement disorders do not appear to be a factor in tiospirone administration. No hint of such side-effects have been seen at the doses used in the present study. Tiospirone also has been demonstrated to possess good analgesic activity in several animal test models of analgesia such as the standard mouse hot plate and phenylquinone writhing tests, and in rats in formalin, and footshock tests. This profile indicates that tiospirone would also be useful against some non-vascular headache types, such as muscle contraction headache, for which analgesics are widely used therapies.

Taken together, these data demonstrate that tiospirone is an effective prophylactic treatment for alleviation of vascular headache. Clinical and preclinical test data of tiospirone have not indicated any drug dependency relationship or limiting side effects after extended use at higher dose levels than described in the present headache study. Therefore, tiospirone offers a significant advantage over most other agents used to treat vascular headache.

The process of the present invention then essentially involves administration of tiospirone or a pharmaceutically acceptable acid addition salt thereof, to a human in need of such treatment for alleviation of vascular headache or a vascular-related subtype and/or relief of pain. Pharmaceutically acceptable acid addition salts of tiospirone and methods of pharmaceutical formulation are described in the patent of Temple, Jr. U.S. Pat. No. 4,411,901 which is incorporated herein in its entirety by reference.

Administration of tiospirone according to the present invention may be by the parenteral, including intramuscular, intravenous, subcutaneous, transnasal and transdermal; oral and rectal routes. The oral route is preferred, however. It is understood that the dosage and dosage regimen must, in each case, be carefully adjusted, utilizing sound professional judgment and considering the age, weight and condition of the recipient, and the route of administration. The clinical oral dosage range is expected to be in the range of about 40 to 200 mg per day, generally given in divided doses. In some instances, a sufficient therapeutic effect can be obtained at lower doses while in others, larger doses will be required. Since the dosage should be tailored to the individual patient, the usual practice is to commence with a dose of about 20 to 25 mg administered two or three times a day and then to increase the dose every 2 or 3 days until the desired response is seen or side effects are exhibited. Single daily dosage may be applicable in some instances, but division of the daily dose into 2 or 3 portions is preferred.

What is claimed is:

1. A method for alleviation of vascular and vascular-related headache comprising migraine, cluster, toxic vascular, hypertensive, muscle-contraction and combined or mixed headaches which method comprises administering a non-toxic therapeutically effective dose of tiospirone or a pharmaceutically acceptable acid addition salt thereof to a human in need of such treatment.

2. The method of claim 1 wherein migraine headache is the vascular headache.

3. The method of claim 1 wherein cluster headache is the vascular headache.

4. The method of claim 1 wherein muscle-contraction headache is the vascular-related headache.

5. The method of claim 1 wherein combined headache is the vascular headache.

6. The method of claim 1 wherein tiospirone hydrochloride is employed and dosage is by the oral route.

7. The method of claim 6 wherein said human is an adult and a daily dose of from about 40 mg to 200 mg is employed.

8. The method of claim 6 wherein said daily dose is divided and administered b.i.d.

9. The method of claim 6 wherein said daily dose is divided and administered t.i.d.

10. A method for alleviation of pain which method comprises administering a non-toxic analgesic-effective dose of tiospirone or a pharmaceutically effective acid addition salt thereof to a human in need of such treatment.

* * * * *